US00PP21895P2

(12) United States Plant Patent
Hurd

(10) Patent No.: US PP21,895 P2
(45) Date of Patent: May 3, 2011

(54) ***DIANTHUS* PLANT NAMED 'POMEGRANATE KISS'**

(50) Latin Name: ***Dianthus* hybrid**
Varietal Denomination: Pomegranate Kiss

(75) Inventor: Kevin Hurd, Zeeland, MI (US)

(73) Assignee: Walters Gardens Inc., Zealand, MI (US)

( * ) Notice: Subject to any disclaimer, the term of this patent is extended or adjusted under 35 U.S.C. 154(b) by 0 days.

(21) Appl. No.: 12/462,746

(22) Filed: Aug. 7, 2009

(51) Int. Cl.
*A01H 5/00* (2006.01)

(52) U.S. Cl. ..... Plt./272

(58) Field of Classification Search ..... Plt./272
See application file for complete search history.

*Primary Examiner* — Susan B McCormick Ewoldt

(57) ABSTRACT

The new and distinct cultivar of perennial Carnation or Pinks, *Dianthus* plant named 'Pomegranate Kiss' with long-blooming, fragrant, highly-double flowers, petals with a deep magenta base and irregular rose pink splashing in the center or petal margins. *Dianthus* 'Pomegranate Kiss' is tolerant of high temperatures and resists high temperatures and center die-out.

2 Drawing Sheets

Botanical denomination: *Dianthus* hybrid.

Cultivar designation: 'Pomegranate Kiss'.

BACKGROUND OF THE INVENTION

The present invention relates to the new and distinct cultivar of *Dianthus* or Pinks from the genus *Dianthus* and given the cultivar name 'Pomegranate Kiss'. The new plant was the result of an intentional cross in May of 2006 by Kevin A. Hurd between 'Double Spotty' U.S. Plant Pat. No. 13,884 as the seed parent and 'Eastern Star' U.S. Plant Pat. No. 14,437 (also known as 'Red Dwarf') as the pollen parent. The new hybrid was first isolated from trials at a nursery in Zeeland, Mich. during the summer of 2007. *Dianthus* 'Pomegranate Kiss' has been asexually propagated at the same nursery in Zeeland, Mich. using traditional shoot tip cutting procedures and found to reproduce plants that are identical and exhibit all the identical characteristics of the original plant.

SUMMARY OF THE INVENTION

The present invention has not been evaluated under all possible environmental conditions. The phenotype may vary with variations in environment including: growing temperature, available sunlight, nutrients, water, etc. without a change in the genotype of the plant. The new plant is distinct from its parents and all other *Dianthus* known to the applicant in the following combined traits:

1. Double flowers with high petal counts.
2. Unique floral color pattern.
3. High heat tolerance.
4. Floriferous habit.
5. Vigorous growth and excellent habit.
6. Compact, fine-textured, blue-green foliage.

Cultivar Comparison Table

| Cultivar | Flower color | Flower pattern | Flower size |
|---|---|---|---|
| 'Apple Slice' application No. 12/462,743 | pink | dark wine edge and rim | 4.5 cm |
| 'Black Cherry Wild' application No. 12/462,742 | burgundy | solid | 4.0 cm |
| 'Coconut Punch' application No. 12/462,744 | white | burgundy edge with white rim | 3.5 cm |
| 'Double Spotty' U.S. Plant Pat. No. 13,884 | burgundy | white picotee edge and white spots | 4.0 cm |
| 'Dragon Fruit' application No. 12/462,745 | fuchsia pink | red jagged purple bar | 3.5 cm |
| 'Pomegranate Kiss' application No. 12/462,746 | burgundy | Irregular pink splashing on margin or center | 3.2 cm |
| 'Cranberry Ice' U.S. Plant Pat. No. 18,342 | pink | dark wine edge and rim | 3.3 cm |
| 'Devon Siskin' U.S. Plant Pat. No. 14,377 | light pink | magenta edge with burgundy base | 4.0 cm |
| 'Feuerhexe' (not patented) | pink | solid | 4.0 cm |
| 'Devon Xera' U.S. Plant Pat. No. 14,895 | red | crimson eye | 3.0 cm |
| Red Dwarf' U.S. Plant Pat. No. 14,437 | red | crimson eye | 3.5 cm |
| 'Sangria Splash' application No. 12/462,741 | fuchsia pink | crimson ring with pink splashing and center | 3.0 cm |
| 'Spangled Star' U.S. Plant Pat. No. 13,029 | scarlet red | small white spots and white picotee edge | 4.0 cm |

| Cultivar | Petal margin | Petal # | Plant height in flower |
|---|---|---|---|
| 'Apple Slice' application No. 12/462,743 | dark wine margin | 20 to 24 | 22 cm |
| 'Black Cherry Wild' application No. 12/462,742 | light rose margin | 16 to 20 | 22 cm |
| 'Coconut Punch' application No. 12/462,744 | reddish purple margin | 14 to 30 | 28 cm |

-continued

| Cultivar Comparison Table | | | |
|---|---|---|---|
| 'Double Spotty' U.S. Plant Pat. No. 13,884 | white | 15 to 20 | 17 to 30 cm |
| 'Dragon Fruit' application No. 12/462,745 | self | 14 to 22 | 20 cm |
| 'Pomegranate Kiss' application No. 12/462,746 | irregular pink splashing | 16 to 22 | 16 cm |
| 'Cranberry Ice' U.S. Plant Pat. No. 18,342 | dark wine margin | 5 | 20 to 25 cm |
| 'Devon Siskin' U.S. Plant Pat. No. 14,377 | magenta edge | 5 | 10 cm |
| 'Feuerhexe' (not patented) | self | 5 | 10 to 12 cm |
| 'Devon Xera' U.S. Plant Pat. No. 14,895 | self | 5 | 15 to 20 cm |
| Red Dwarf' U.S. Plant Pat. No. 14,437 | self | 5 | 20 to 25 cm |
| 'Sangria Splash' application No. 12/462,741 | crimson with pink splashing | 5 | 30 cm |
| 'Spangled Star' U.S. Plant Pat. No. 13,029 | white picotee edge | 5 | 17 to 27 cm |

BRIEF DESCRIPTION OF THE DRAWINGS

The photographs of the new invention demonstrate the overall appearance of the plant including the unique traits. The colors are as accurate as reasonably possible with color reproductions. Some slight variation of color may occur as a result of lighting quality, intensity, wavelength, direction or reflection.

DETAILED DESCRIPTION OF THE PLANT

Figure 1:
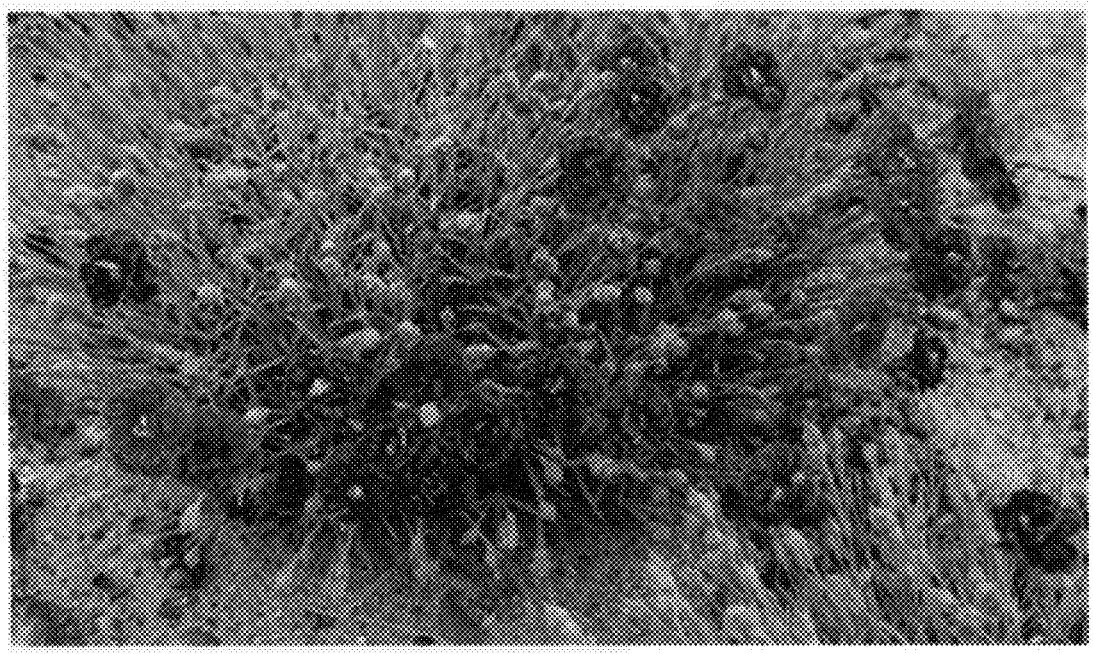
FIG. 1 shows the new two-year old plant in flower.
Figure 2:
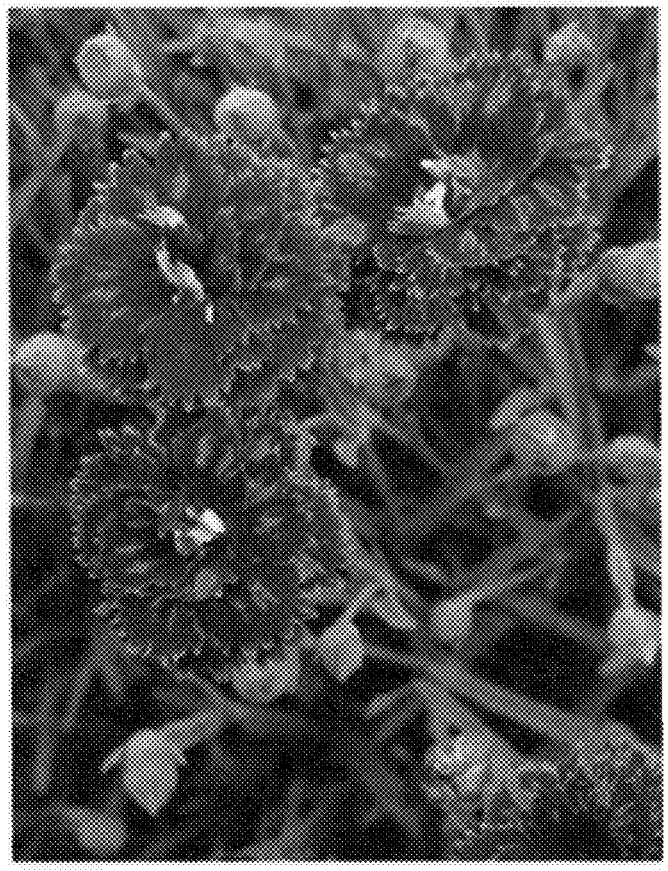
FIG. 2 shows a close-up of the flower and bud.
Figure 3:
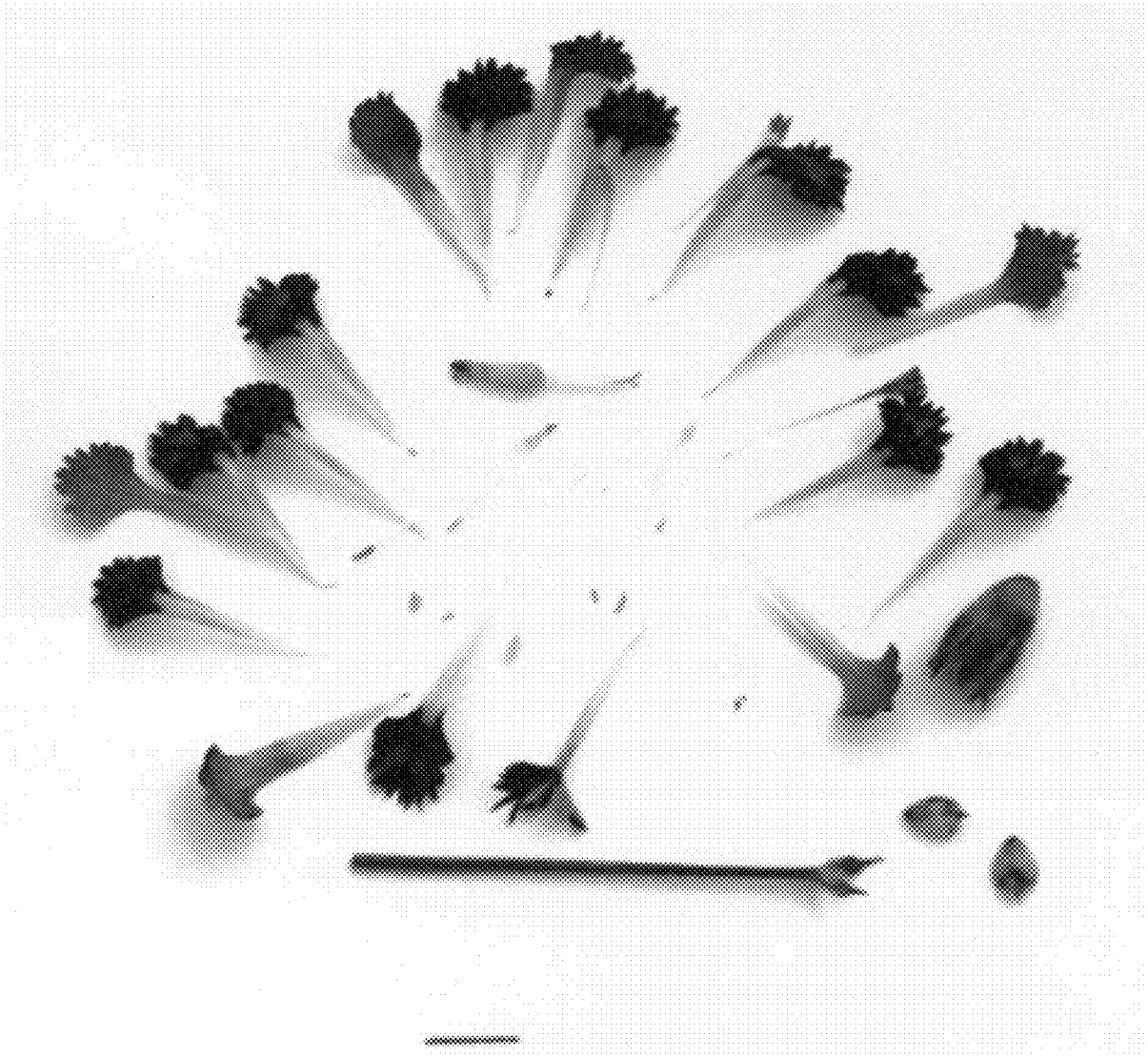
FIG. 3 shows the dissected flower of the new plant together with capsule and seeds.

The following detailed description of the new plant is based on observations of several two-year old plants in open-field, full-sun conditions in Zeeland, Mich. with supplemental watering, light additions of fertilizer and free of other plant growth regulators. All color usage is in reference to the 2001 edition of The Royal Horticultural Colour Chart except where common dictionary terms are used.

Botanical classification: *Dianthus* hybrid;

Parentage: 'Double Spotty' (female) times 'Eastern Star' (male);

Plant description:

*Habit.*—Cespitose, herbaceous, evergreen perennial; stems proximally branched, erect; height of foliage about 12 cm and 35 cm across; height with flowers is about 16 cm; Root system; fibrous.

Foliage:

*Leaf type.*—Simple, linear, opposite, decussate, sessile, glabrous, glaucous on adaxial and abaxial; acute apex; base decurrent, adpressed along stem and somewhat perfoliate; no fragrance detected.

*Leaf dimensions.*—About 3.5 cm long and 2.5 mm wide.

*Leaf color.*—Nearest RHS 119B adaxial and abaxial sides.

*Venation.*—Finely reticulate, coloration same as that of leaf top and bottom.

*Stems.*—Erect to arching, terete, glabrous, glaucous, proximally branching at 2 to 3 nodes.

*Stem size.*—About 16 cm long and 2 mm wide at base.

*Stem color.*—Nearest RHS 122B.

*Branching.*—Numerous from lower leaf axils; about 200 per plant.

*Nodes.*—3 mm across, RHS N147D.

*Internodes.*—3.5 cm apart.

Inflorescence:

*Type.*—Terminal, cymose, erect.

*Flowers per stem.*—Usually 3.

*Pedicel.*—Glaucous, glabrous, terete.

*Pedicel size.*—Usually 2 cm long and 2 mm diameter.

*Pedicel color.*—Nearest RHS 122A.

Flowers:

*Type.*—Salviform, completely double, symmetrical.

*Dimension.*—About 3.2 cm across and extending about 1.5 cm above calyx.

*Flower bud shape.*—Rhomboid to ovoid.

*Flower bud size one day prior to opening.*—About 1.7 cm long and 0.7 cm wide.

*Flower bud color.*—Glaucous, between RHS 141B and RHS 141C with anthocyanin patches between RHS 187B and RHS N187B.

*Flower period.*—Beginning late May and flowering until frost in the fall with a short 2 week rest after the initial bust.

*Flower lasting quality.*—About one week on or off the plant.

*Flower fragrance.*—Light, sweet spicy, clove-like.

*Petals.*—16 to 22, consisting of a rounded blade or limb and a claw (enclosed completely within the calyx), obovate, apex dentate with dentations 3 mm deep, bearded with minute hairs mostly on the center of the adaxial surface, bent outwardly to nearly a ninety degree angle; deep magenta-colored limb base on adaxial side with an irregular pink splashing on margin or in center.

*Petal color.*—Adaxial limb: deep magenta limb darker RHS 59A, irregular pink margin and limb center splashing between RHS 63A and RHS 58A; adaxial claw: nearest RHS N144C; abaxial limb: Nearest RHS 64A with irregular lighter spots or margin of nearest RHS 63B; abaxial claw: Nearest RHS N144D.

*Dimension.*—Variable, 2.8 cm long including claw and limb; larger petal limb to 1.2 cm across and 1.5 cm long, smaller limbs to 3 mm across and 6 mm long; claws range from 0.7 cm to 1.5 cm long and 2 mm to 6 mm wide about 3 mm from limb.

*Calyx.*—Glabrous, glaucous, five-toothed corolla tube fused in proximal 1.3 cm; about 1.7 cm long and 0.8 cm in diameter; RHS 147D with anthocyanin tinting of RHS N77C.

*Peduncle.*—Glabrous, glaucous, terete, 16 cm long and 2 mm diameter; RHS N138D with anthocyanin of RHS N77C.

*Bracts.*—Two, opposite, broadly obtuse with rounded apex, about 7 mm long and 10 mm wide; RHS N138C in the center, lighter than RHS 138D at base and margins.

*Bracteoles.*—Two, opposite, lanceolate, sharply acute apex, bases joined at stem; about 10 mm long and 4 mm wide; glaucous, RHS N138C at apex and center, lighter than RHS 138D at base and margins.

*Androecium.*—Stamens usually 10, filaments variable in length from 0.7 to 2.0 cm long, less than 1 mm diameter; pale green lighter than RHS 11D; anther oblong to 3.2 mm long and 1.0 mm wide, RHS 11C; pollen rare, pollen color RHS 11D.

*Gynoecium.*—Style split in two above ovary, pistil 2 cm long and about 1 mm diameter, lighter than RHS 11D except for distal 8 mm which are gradually darken to RHS N79C; stigma RHS N79B.

*Ovary.*—Superior, ovoid; 8 mm long and 3 mm wide; RHS 145A at distal end and between RHS 145 D and RHS 145 C at proximal end.

Seed: Seed has not been observed;

Capsule: Ovoid to cylindrical, opening by 4 teeth, about 2 cm long and 8.5 mm diameter, between RHS 197B and RHS 197 C;

Comparison varieties: The new plant is distinct from its parents and all other *dianthus* known to the inventor in that the new plant has double flowers unlike 'Eastern Star', has a dark magenta flower with irregular rose pink splashing in the petal center, and has more finely textured foliage. The nearest comparison plant would be co-pending application Ser. No. 12/462,742 'Black Cherry Wild' which has similar base colored petals but without the rose pink splashing. The new plant also has deeper dentations in the petals than co-pending application Ser. No. 12/462,742 'Black Cherry Wild'.

Disease resistance: The new plant is resistant to center die out from fungus or high temperatures. The plant grows best with adequate moisture and well-drained soil, but is able to tolerate high temperatures and some drought once established. Hardiness at least from USDA zone 4 through zone 9.

I claim:

1. A new and distinct cultivar of perennial Carnation or Pinks, *Dianthus* plant named 'Pomegranate Kiss' as herein described and illustrated, with long-blooming, fragrant, highly-double flowers, petals with a deep magenta base and irregular rose pink splashing in the center or petal margins, tolerant of high temperatures, resistant to center die-out, and suitable as a garden ornamental, potted plant and for cut flower arrangements.

* * * * *